United States Patent [19]
Zuk

[11] Patent Number: 5,988,003
[45] Date of Patent: *Nov. 23, 1999

[54] RELATIVE HUMIDITY CONTROL SYSTEM FOR CORROSION TEST CHAMBER

[75] Inventor: Boris Zuk, Parma, Ohio

[73] Assignee: The Singleton Corporation, Cleveland, Ohio

[*] Notice: This patent is subject to a terminal disclaimer.

[21] Appl. No.: 09/130,762

[22] Filed: Aug. 7, 1998

Related U.S. Application Data

[63] Continuation of application No. 08/800,476, Feb. 14, 1997, Pat. No. 5,824,918.

[51] Int. Cl.⁶ .............................. G01N 7/16; G01N 17/00
[52] U.S. Cl. ............................ 73/865.6; 73/29.01; 73/86
[58] Field of Search ................ 73/865.6, 29.01, 73/86, 147

[56] References Cited

U.S. PATENT DOCUMENTS

| | | | |
|---|---|---|---|
| 3,594,128 | 7/1971 | Singleton | 73/865.6 |
| 3,886,791 | 6/1975 | Grossman | 73/865.6 |
| 3,987,133 | 10/1976 | Andra | 261/130 |
| 4,622,049 | 11/1986 | Abernathy et al. | 73/865.6 |
| 4,643,351 | 2/1987 | Fukamachi et al. | 73/335.02 |
| 4,751,844 | 6/1988 | Matsushtia | 73/147 |
| 4,770,031 | 9/1988 | Roth et al. | 73/147 |
| 4,779,468 | 10/1988 | Susuki | 73/865.6 |
| 4,852,389 | 8/1989 | Mayer et al. | 73/38 |
| 5,463,940 | 11/1995 | Cataldo | 99/476 |
| 5,476,636 | 12/1995 | Tomiita et al. | 73/865.6 |
| 5,503,032 | 4/1996 | Tikhtman et al. | 73/865.6 |
| 5,824,918 | 10/1998 | Zuk | 73/865.6 |

Primary Examiner—Hezron Williams
Assistant Examiner—Chad Soliz
Attorney, Agent, or Firm—Fay, Sharpe, Fagan, Minnich & McKee, LLP

[57] ABSTRACT

A method and apparatus for controlling the level of relative humidity within a corrosion test apparatus is disclosed. The corrosion test apparatus includes a testing chamber, an atomizer which fogs the testing chamber with de-ionized water, a sensor which senses a relative humidity level within the testing chamber, a humidifying valve coupled to the atomizer which regulates a supply of pressurized air to the atomizer, and a controller coupled to the sensor and to the humidifying valve. The controller includes a heating control loop mechanism which generates an output signal proportional to a differential between a relative humidity set point and the relative humidity level. The humidifying valve regulates the supply of operating medium to the atomizer based on the output signal. The atomizer regulates the amount of operating liquid fogged into the test chamber based on the supply of operating medium received from the humidifying valve. The corrosion test apparatus also includes a dehumidifying valve which regulates a supply of ambient air to the testing chamber based on the differential between the relative humidity set point and the relative humidity level, and a passive, low-cost, low maintenance air amplifier coupled to the dehumidifying valve which draws ambient air into the testing chamber.

20 Claims, 2 Drawing Sheets

RELATIVE HUMIDITY CONTROL SYSTEM FOR CORROSION TEST CHAMBER

CROSS REFERENCE TO RELATED APPLICATIONS

This application is a continuation of U.S. patent application Ser. No. 08/800,476, filed Feb. 14, 1997, now U.S. Pat. No. 5,824,918.

BACKGROUND OF THE INVENTION

The present invention relates to the corrosion testing art. It finds particular application in conjunction with accelerated corrosion testing chambers and will be described with particular reference thereto. However, it should be appreciated that the present invention also finds application in conjunction with other types of environmental testing systems and applications which require control or regulation of relative humidity.

Corrosion testing is required of many items which must meet corrosion resistance standards set by various governmental agencies and industrial concerns. The testing of the ability of various products to withstand corrosive influences is frequently conducted by accelerated exposure techniques. The methods utilize a test cabinet into which parts to be tested are placed. A corrosive atmosphere or environment is then introduced into the cabinet at specified levels for specified periods of time. Exposed items are then removed from the cabinet and scrutinized for signs of corrosion, structural breakdown and the like. The corrosion test cabinets must be capable of maintaining rigid standards and capable of repetition under identical conditions.

Present corrosion resistance standards, such as the proposed SAE (Society of Automotive Engineers) J2334 standard or the General Motors 9540-P standard, specify that parts or items to be tested must be exposed to a number of different corrosive influences in specified amounts for specified periods of time. In particular, parts to be tested must be exposed to a number of salt spray (fog) cycles, humidity cycles and drying cycles. However, known corrosive testing cabinets do not have the capability to deliver multiple corrosive influences to the parts to be tested within a single testing chamber.

In particular, known corrosive salt spray (fog) testing chambers can not regulate, control or maintain specified levels of relative humidity within a testing chamber during humidity and drying cycles as required by present corrosion resistance standards. Thus, to comply with present corrosion resistance standards, it has been necessary to move the parts to be tested from one corrosion testing cabinet to another when the testing cycle (i.e. the type of corrosive influence) changes.

Accordingly, it has been considered desirable to develop a new and improved corrosion testing chamber which meets the above-stated needs and overcomes the foregoing difficulties and others while providing better and more advantageous results.

SUMMARY OF THE INVENTION

In accordance with a first aspect of the present invention, a corrosion testing apparatus is disclosed. The corrosion test apparatus includes a testing chamber, an atomizer which fogs the testing chamber with an operating fluid, a sensor which senses a relative humidity level within the testing chamber, a humidifying valve coupled to the atomizer which regulates a supply of an operating medium to the atomizer, and a controller coupled to the sensor and to the humidifying valve. The controller includes a heating control process loop which generates an output signal proportional to a differential between a relative humidity set point and the relative humidity level. The humidifying valve regulates the supply of operating medium to the atomizer based on the output signal. The atomizer regulates the amount of operating liquid fogged into the test chamber based on the supply of operating medium received from the humidifying valve.

In accordance with a second aspect of the present invention, a method of regulating relative humidity within a corrosion testing apparatus is disclosed. The method includes the steps of sensing a relative humidity level within the testing apparatus, generating an output signal proportional to a differential between a relative humidity set point and the relative humidity level, and controlling a flow of operating medium supplied to an atomizer based on the output signal.

In accordance with a third aspect of the present invention, a corrosion testing apparatus is disclosed. The corrosion test apparatus includes a testing chamber, an atomizer which fogs the testing chamber with an operating fluid, a sensor which senses a relative humidity level within the testing chamber, and a humidifying valve which regulates a supply of an operating medium to the atomizer based on a differential between a relative humidity set point and the relative humidity level.

One advantage of the present invention is that it permits salt spray (fog), humidity, and drying cycles to be carried out within the same testing chamber of a corrosion testing apparatus.

Another advantage of the present invention is that it eliminates the practice of moving parts to be tested from one testing chamber to another testing chamber when the corrosive influence changes (i.e. when a humidity testing cycle is specified).

Another advantage of the present invention is that it permits compliance with present corrosion resistance standards such as the proposed SAE J2334 standard or the GM 9540-P standard.

Another advantage of the present invention is that it utilizes a low-cost, low-maintenance, passive air amplifier to introduce ambient air into the testing chamber.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
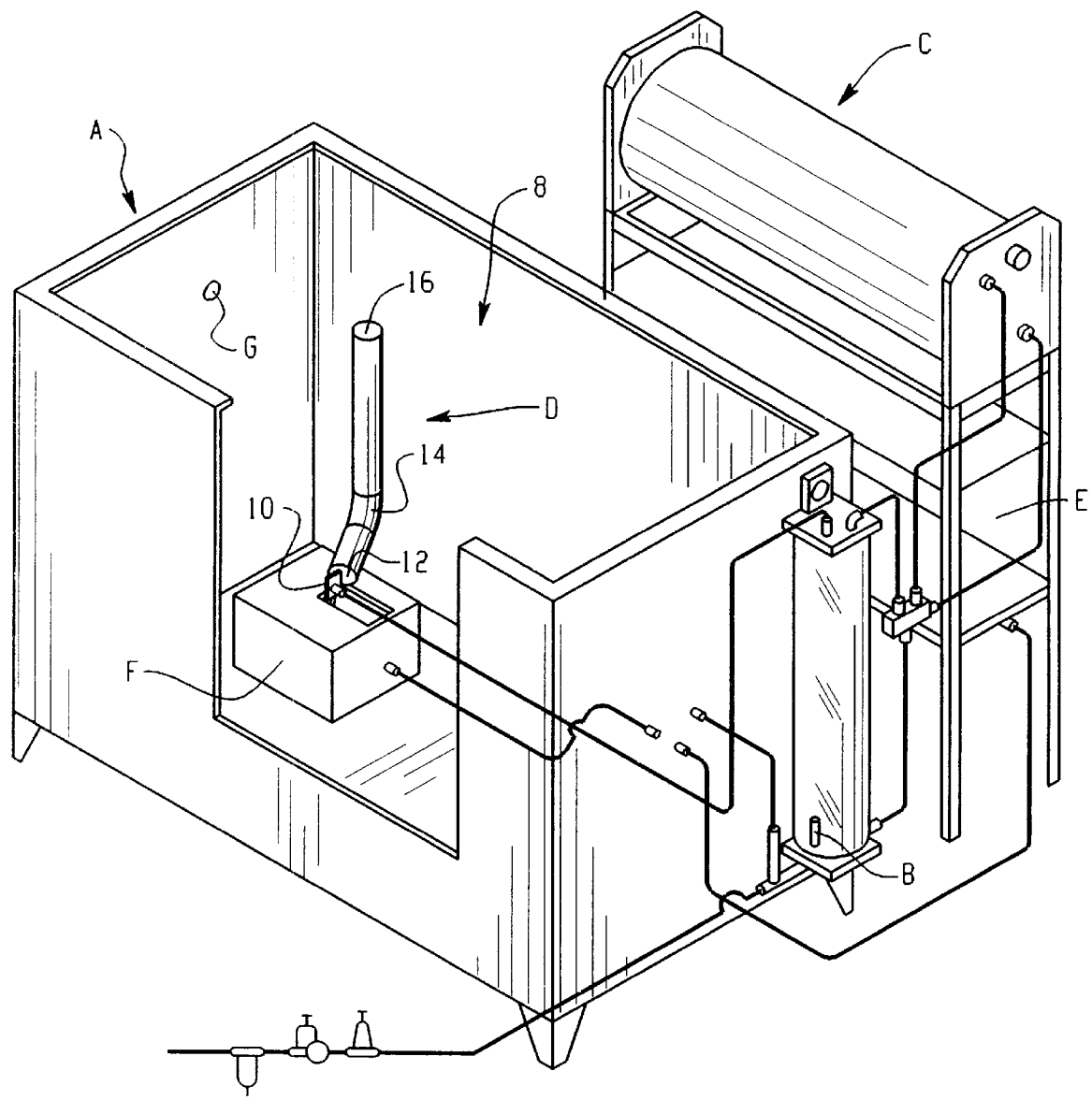
FIG. 1 is a perspective view of an exemplary corrosion testing cabinet which delivers salt spray (fog) to a testing chamber.

With reference to FIG. 1, an exemplary corrosion test cabinet A subjects specimens, parts or items to corrosive salt spray (fog) in accordance with numerous corrosion resistance standards promulgated by governmental and industrial concerns. A bubble tower B and associated reservoir C supply humidified air to a fog generator, which includes a fog tower D positioned within a testing chamber 8 of the cabinet A. A salt solution reservoir E feeds a reservoir F of the fog generator with salt solution to be atomized as corrosive fog by the compressed, humidified air from the bubble tower B.

The bubble tower B, reservoir C, fog tower D, salt solution reservoir E and reservoir F cooperate to deliver a corrosive salt spray (fog) to the testing chamber 8 during salt spray (fog) cycles in compliance with present corrosion testing procedures. The objective of salt spray (fog) testing is to expose the parts to be tested to corrosive salt spray without concern for controlling or regulating the level of relative humidity within the testing chamber 8. That is, introducing salt spray (fog) into the test chamber 8 during salt spray (fog) testing cycles necessarily and unavoidably results in a high level of relative humidity (i.e. 95%–100%) within the testing chamber.

Briefly, the testing chamber 8 is saturated with corrosive salt spray (fog) by an atomizer nozzle 10 which supplies a fine mist to an inlet 12 of the fog tower D. A source of pressurized air (not shown) is combined with water and temporarily retained in the bubble tower B in a known manner before transmission to the atomizer nozzle 10.

Salt solution is drawn by venturi effect or other conventional manner from the reservoir F and atomized as corrosive salt fog by the pressurized, humidified air. The corrosive salt spray (fog) exits the atomizer nozzle 10 and impinges upon an elbow-shaped baffle 14 of the fog tower D to prevent any liquid or unatomized droplets from being emitted from the outlet 16 of the fog tower D and into the testing chamber 8.

The tower outlet 16 is desirably positioned near the top of the testing chamber 8 and the corrosive fog is distributed axially upward and radially outward due to the continuous force of fog emitted by the atomizer nozzle 10. An exhaust outlet or fitting G is provided through a side wall of the corrosion test cabinet A to maintain a constant test environment in the chamber 8. A clear plastic or similar material top (not shown) may be provided on the cabinet A for visual monitoring of the specimen testing.

The atomizer nozzle 10 is usually directed so that none of the corrosive spray can directly impinge on the test specimens placed within the cabinet A. That is, only small, fine particles can exit from the tower outlet 16. Suitable racks (not shown) or other suspension means are provided for placement of the tested specimens at various predetermined locations within the testing chamber 8. Preferably, the racks are adjustable so that the specimens can be located at different lateral and axial positions varying in distance from the tower outlet 16.

The test specimens are then subjected to a salt spray (fog), or another corrosive liquid or gas, for predetermined periods of time. The salt solution from the salt solution reservoir E is automatically supplied to the reservoir F and eliminates the necessity of constant monitoring of corrosion tests.

The test cabinet A may also be equipped with recording instruments which monitor the humidity and/or temperature within the testing chamber 8. Further details of the structure and operation of a conventional corrosion test cabinet may be found in commonly assigned U.S. Pat. Nos. 3,557,819, 3,594,128, 4,189,472 and 4,752,466.

Figure 2:
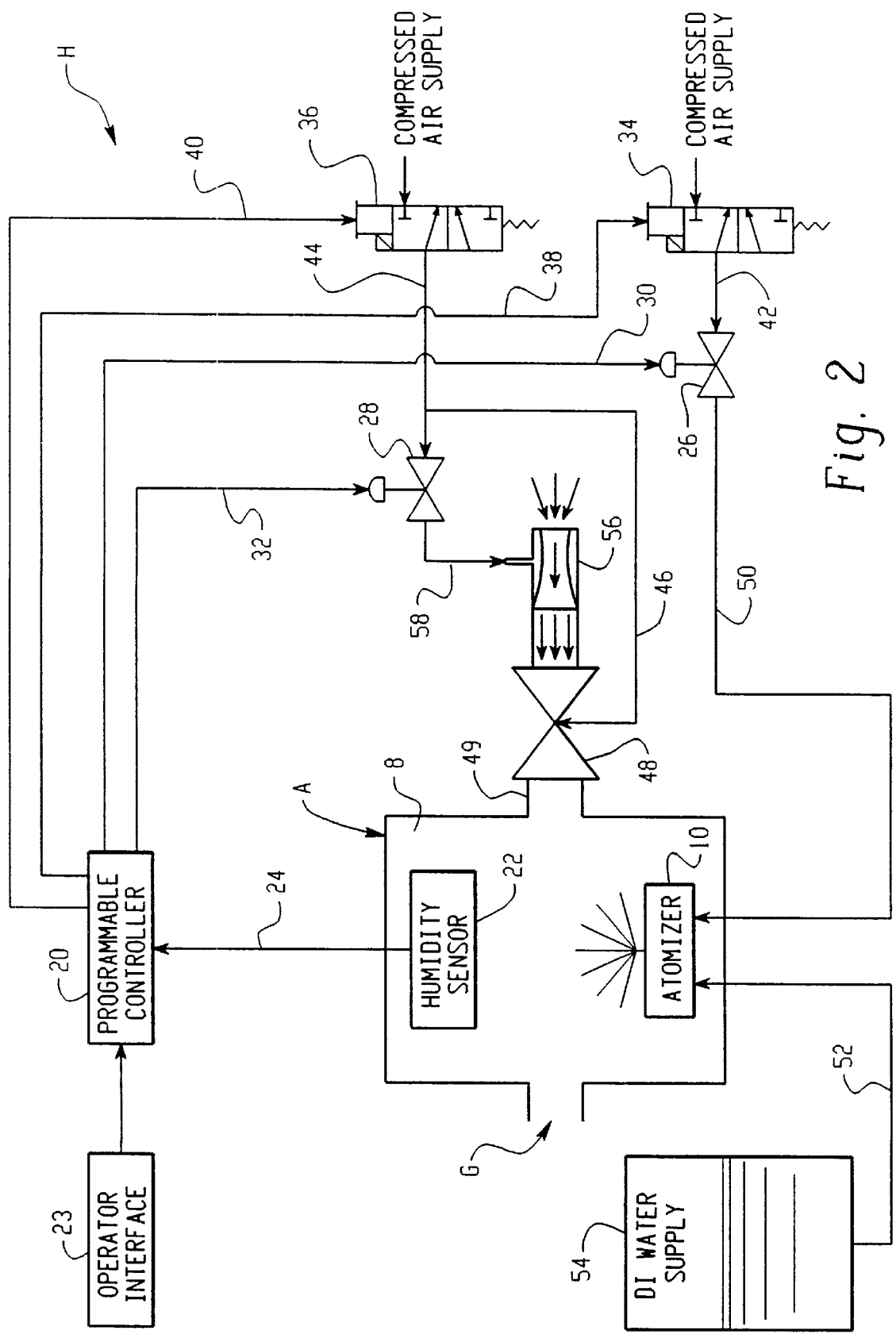
FIG. 2 is a schematic diagram of relative humidity control system for use with the corrosion testing cabinet of FIG. 1.

Referring now to FIG. 2, a relative humidity control system H for use with the corrosion test cabinet A is shown. Relative humidity is defined as a ratio, in percent, of the moisture actually in the air to the moisture the air would hold if the air were saturated at the same temperature and pressure.

The relative humidity control system H regulates the level of relative humidity within the test chamber 8 only during humidity and drying cycles. That is, the relative humidity control system H operates independent of the salt spray control system. The bubble tower B and salt solution reservoir E are not operative during humidity and drying cycles.

The relative humidity control system H includes a conventional programmable controller or small logic controller (SLC) 20 with proportional integral derivative (PID) instruction capability. In a preferred embodiment, the controller 20 includes a minimum of one (1) combination analog input (2-point)/output (2-point) module, and one (1) 120 VAC relay output (4-point) module.

The relative humidity control system H also includes a humidity transmitter or analog source 22 at least partially mounted within the testing chamber 8 for sensing the level of relative humidity within the testing chamber. An exemplary humidity transmitter 20 suitable for use in the present invention is the Model HMM 20D Humidity Module which is commercially available from Vaisala Inc. of Woburn, Mass.

The controller 20 feeds +24 VDC to the humidity transmitter 22. An output signal line 24 couples an output signal from the humidity transmitter 22 to the analog input side of the combination analog input/output module of the controller 20. A relative humidity set point may be programmed into the controller 20 through an operator interface 23 coupled to the controller 20.

Two (2) low voltage current to pressure (I-to-P) transducers 26, 28 are connected directly to the combination analog input/output module of the controller 20 via output control lines 30, 32, respectively. An exemplary current-to-pressure transducer 26, 28 suitable for use in the present invention is the Series X55-600 I to P transducer which is commercially available from Ronan Engineering Company of Woodland Hills, Calif.

Two (2) solenoid valves 34, 36 are connected to separate output terminals of the controller 120 VAC relay module via output control lines 38, 40, respectively. A supply of compressed air (approximately 90 PSI) is connected to each of the two solenoid valves 34, 36. A first pneumatic supply line 42 connects an air output of the solenoid valve 34 to an air input of the current to pressure transducer 26, designated hereafter as a humidifying valve.

A second pneumatic supply line 44 connects an air output of the solenoid valve 36 to an air input of the current to pressure transducer 28, designated hereafter as a dehumidifying valve. A pneumatic control line 46 connects the air output of the solenoid valve 36 to a 2-way, spring return, ball valve 48 which is positioned in-line with an air inlet duct 49 that communicates with the testing chamber 8.

An air output of the humidifying valve 26 is connected to the atomization nozzle 10 (FIG. 1) via a regulated pneumatic supply line 50. A de-ionized water supply line 52 connects a source of de-ionized water 54 to a solution side of the atomization nozzle 10 so that the atomization nozzle 10 can create fog thereby increasing the level of relative humidity in the testing chamber 8.

In particular, the testing chamber 8 is saturated with fog by the atomizer nozzle 10 which supplies a fine mist to the inlet 12 of the fog tower D. The de-ionized water is drawn by venturi effect or other conventional manner from the supply line 52 and atomized as fog by the pressurized air supplied from the regulated pneumatic supply line 50.

The fog exits the atomizer nozzle 10 and impinges upon the elbow-shaped baffle 14 of the fog tower D to prevent any liquid or unatomized droplets from being emitted from the outlet 16 of the fog tower D and into the testing chamber 8, in the same manner described above with regard to the salt spray (fog) testing cycles.

An air output of the dehumidifying valve 28 is connected to an air amplifier 56 via a pneumatic control line 58. The air amplifier 56 is positioned in-line with the air inlet duct 49 and in series with the 2-way ball valve 48. An exemplary air amplifier 56 suitable for use in the present invention is the Model 901 or 901B Transvector Jet which is commercially available from Vortec Corporation of Cincinnati, Ohio.

Energizing the solenoid valve 36 opens the 2-way ball valve 48, thereby allowing ambient air to flow through the air amplifier 56 and into the testing chamber 8. The positive flow of ambient air into the testing chamber 8 forces humidified air out of the testing chamber 8 through the exhaust port G, thus decreasing the relative humidity in the testing chamber 8.

The operation of the relative humidity control system will now be discussed. In a PID closed-loop control system, the concept is to hold a process variable at a desired set point. In the embodiment being described, the process variable is the actual level of relative humidity within the testing chamber 8 that is measured, calculated, extrapolated, or otherwise determined by the relative humidity control system H. The set point is the desired level of relative humidity to be maintained within the testing chamber 8.

Two types of PID control loops are commonly referred to as a heating loop and a cooling loop. In both heating and cooling loops, the greater the differential between the set point and process variable, the greater the output signal. Where a heating control loop raises a process value to a set point, the cooling control loop performs the opposite function and lowers the process value to the desired set point.

The relative humidity control system H uses both the heating and cooling PID loop control systems in the ladder logic of a control program. For example, if the relative humidity set point is 95%, and the process variable (actual relative humidity value as determined by the humidity sensor 22) is 70% relative humidity, the controller 20 sends a 120 VAC signal to the solenoid valve 34 via control line 38, hence opening the valve 34, and allowing a supply of compressed air to be delivered to the humidifying valve 26.

The controller 20 also sends a variable, controlled output signal on control line 30 to the humidifying valve 26. The magnitude of the output signal (e.g. magnitude of current flow) from the controller 20 is proportional to the control output of the heating PID control loop. The humidifying valve 26 opens in proportion to the magnitude of the output signal to supply a regulated amount of compressed air to the atomizer via the regulated pneumatic supply line.

The compressed air activates the atomizer nozzle 10 and fogs the testing chamber 8 with the deionized water supplied from the water supply line 52, thus increasing the relative humidity level within the testing chamber 8. Once the process variable (e.g. relative humidity level) reaches the set point, the output signal on control line 30 is reduced to a minimum, or ends. Likewise, the output signal on the control line 38 stops and the solenoid valve 34 is deactivated thereby stopping the supply of compressed air to the humidifying valve 26.

The same, but opposite, is true if the set point remained at 95%, and the process variable (e.g. relative humidity level) was 100%. In this instance, the controller 20 energizes or activates the air supply solenoid valve 36, thus activating the dehumidifying valve 28 and the 2-way ball valve 48. A controlled output signal on control line 32 is sent to the dehumidifying valve 28 in proportion to the control output from the cooling PID control loop.

At the same time, the dehumidifying valve 28 supplies a controlled or regulated amount of pressurized air to the air amplifier 56 via pneumatic control line 58. In response, the air amplifier 56 draws outside ambient air into the testing chamber, thus purging the humid air from the testing chamber.

Once the process variable reaches the set point, the output signal on control line 32 is reduced to a minimum, or stopped. Likewise, the output signal on the control line 40 stops and the solenoid valve 36 is deactivated thereby stopping the supply of compressed air to the dehumidifying valve 28 and to the 2-way ball valve 48. When the 2-way ball valve 48 closes, humid air from within the testing chamber is prevented from escaping through the inlet port 49.

The heating control loop and the cooling control loop of the controller 20 operate independently. However, if desired, both control loops may operate simultaneously to regulate the relative humidity level within the testing chamber by properly adjusting or setting the PID parameters associated with the controller 20.

The invention has been described with reference to a preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

For instance, the air amplifier 56 may be replaced with a blower controlled by an input signal proportional to the control output from the cooling PID control loop. Alternatively, a duty cycle of the blower may also be controlled in order to regulate the amount of ambient air introduced into the testing chamber.

In addition, the air amplifier 56 may be replaced with a blower, and the 2-way ball valve may be replaced with a 3-way ball valve. In this embodiment, the blower is either activated or deactivated. The extent of opening of the 3-way ball valve, and hence the amount of ambient air introduced into the testing chamber, is then controlled by an input signal to the 3-way ball valve which is proportional to the control output from the cooling PID control loop.

However, it should be appreciated that the air amplifier 56 of the preferred embodiment provides a superior, low-cost, low-maintenance, passive solution relative to a blower which requires electrical input and which includes actively rotating components which are subject to wear.

Having thus described the preferred embodiment, the invention is now claimed to be:

1. A corrosion testing apparatus comprising:
   a test chamber;
   an atomizer including a nozzle positioned within the test chamber;
   a baffle positioned proximate the atomizer nozzle;
   means for generating corrosive fog within the test chamber by discharging a first atomized operating fluid from the atomizer nozzle during a first test cycle;

means for generating relative humidity within the test chamber by discharging a second atomized operating fluid from the nozzle during a second test cycle occurring prior to or after the first test cycle; and the baffle preventing unatomized operating fluid discharged from the atomizer nozzle from dispersing within the test chamber.

2. The apparatus of claim 1, wherein:

the atomizer further includes an operating fluid port and an operating medium port, and the corrosive fog generating means includes means for supplying a salt solution to the operating fluid port, and means for supplying humidified air to the operating medium port.

3. The apparatus of claim 2, wherein:

the salt solution supplying means includes a reservoir associated with the atomizer and a source of salt solution which feeds into the reservoir, and the humidified air supplying means includes a bubble tower containing a liquid, and a source of pressurized air which bubbles through the liquid prior to being supplied to the operating medium port.

4. The apparatus of claim 1, wherein:

the atomizer further includes an operating fluid port and an operating medium port, and the relative humidity generating means includes means for supplying de-ionized water to the operating fluid port, and means for supplying air to the operating medium port.

5. The apparatus of claim 4, further including means for regulating the level of relative humidity generated within the test chamber during the second test cycle.

6. The apparatus of claim 5, wherein the regulating means includes means for introducing ambient air into the test chamber.

7. The apparatus of claim 5, wherein the regulating means includes means for adjusting the flow of pressurized air supplied to the operating medium port.

8. The apparatus of claim 4, wherein the corrosive fog generating means includes means for supplying a salt solution to the operating fluid port, and means for supplying humidified air to the operating medium port.

9. The apparatus of claim 8, wherein:

the salt solution supplying means includes a reservoir associated with the atomizer and a source of salt solution which feeds into the reservoir, and the humidified air supplying means includes a bubble tower containing a liquid, and a source of pressurized air which bubbles through the liquid prior to being supplied to the operating medium port.

10. The apparatus of claim 1, wherein the relative humidity generating means includes:

a relative humidity level sensor;

a first valve for regulating a flow of operating medium supplied to the atomizer;

a second valve for regulating a supply of ambient air drawn into the testing chamber; and a controller coupled to the sensor, the first valve, and the second valve, the controller including a heating control loop means which generates a first output signal proportional to a differential between a relative humidity set point and a sensed relative humidity level within the test chamber, and a cooling control loop means which generates a second output signal proportional to a differential between the relative humidity set point and the sensed relative humidity level;

the first valve regulating the supply of operating medium to the atomizer based on the first output signal, the second valve regulating the supply of ambient air drawn into the test chamber based on the second output signal, and the atomizer regulating the amount of second atomized operating liquid discharged based on the flow of operating medium supplied to the atomizer.

11. The apparatus of claim 10, further including:

an air amplifier coupled to the second valve which draws ambient air into the test chamber, a ball valve interposed between the air amplifier and an intake aperture of the test chamber, and a solenoid valve which supplies operating medium to the second valve and the ball valve in response to a third output signal received from the controller.

12. The apparatus of claim 11, further including a second solenoid valve which supplies operating medium to the first valve in response to a fourth output signal received from the controller.

13. The apparatus of claim 10, wherein the first and second valves are current-to-pressure transducers.

14. The apparatus of claim 1, wherein:

the baffle includes an inlet, an outlet, and an elbow-shaped intermediate portion, and the operating fluid discharged from the atomizer nozzle impinges upon the elbow-shaped portion to prevent unatomized operating fluid from being emitted from the outlet.

15. The apparatus of claim 1, wherein the first atomized operating fluid is a salt solution and the second atomized operating fluid is de-ionized water.

16. A corrosion testing apparatus comprising:

a test chamber;

an atomizer including a nozzle positioned within the test chamber;

a corrosive fog generator selectively coupled to the atomizer, the corrosive fog generator generating a corrosive fog within the test chamber by discharging a first atomized operating fluid from the atomizer nozzle during a first test cycle; and a relative humidity generator selectively coupled to the atomizer, the relative humidity generator generating relative humidity within the test chamber by discharging a second atomized operating fluid from the nozzle during a second test cycle occurring prior to or after the first test cycle.

17. The apparatus of claim 16, wherein:

the corrosive fog generator includes a corrosive fluid reservoir in communication with the atomizer, and a bubble tower in communication with the atomizer; and the relative humidity generator includes a source of de-ionized water in communication with the atomizer, and a source of pressurized air in communication with the atomizer.

18. The apparatus of claim 17, wherein the relative humidity generator further includes a relative humidity regulator that regulates at least one of i) a flow of ambient air introduce into the test chamber, and ii) a flow of pressurized air supplied to the atomizer.

19. The apparatus of claim 17, further including:

a relative humidity level sensor;

a valve between the source of pressurized air and the atomizer; and a controller connected to the relative humidity level sensor and the valve, the controller generating a valve adjustment signal in response to the relative humidity level sensor to control a flow of pressurized air supplied to the atomizer.

20. The apparatus of claim 16, further including:

a baffle positioned proximate the atomizer nozzle, the baffle preventing unatomized operating fluid discharged from the atomizer nozzle from dispersing within the test chamber.

* * * * *